United States Patent [19]
Morris, Jr. et al.

[11] Patent Number: 6,027,737
[45] Date of Patent: Feb. 22, 2000

[54] TREATMENT FOR OSTEOPOROSIS USING POTASSIUM SALTS

[75] Inventors: R. Curtis Morris, Jr.; Anthony Sebastian, both of San Francisco, Calif.

[73] Assignee: The Regents of the University of California, Oakland, Calif.

[21] Appl. No.: 08/330,235

[22] Filed: Oct. 27, 1994

Related U.S. Application Data

[63] Continuation of application No. 08/023,744, Feb. 25, 1993, abandoned, which is a continuation of application No. 07/805,673, Dec. 12, 1991, abandoned, which is a continuation of application No. 07/420,597, Oct. 17, 1989, Pat. No. 5,171,583, which is a continuation-in-part of application No. 07/260,856, Oct. 21, 1988, abandoned.

[51] Int. Cl.[7] .............................. A61K 9/00; A61K 9/16; A61K 9/20; A61K 9/48
[52] U.S. Cl. .......................... 424/400; 424/451; 424/464; 424/489; 424/439
[58] Field of Search ................................. 424/422, 717, 424/464, 489, 451, 400, 439

[56] References Cited

U.S. PATENT DOCUMENTS

| | | |
|---|---|---|
| 3,541,208 | 11/1970 | Dann . |
| 3,639,585 | 2/1972 | Hesse . |
| 3,821,368 | 6/1974 | Reynolds ................................ 424/128 |
| 4,216,237 | 8/1980 | Smith ...................................... 426/631 |
| 4,772,467 | 9/1988 | Pak ......................................... 424/127 |
| 4,814,177 | 3/1989 | Walsdorf et al. ....................... 424/464 |
| 4,851,221 | 7/1989 | Pak et al. ............................... 424/693 |
| 4,888,182 | 12/1989 | Pak ......................................... 514/891 |
| 5,171,583 | 12/1992 | Morris, Jr. et al. .................... 424/717 |
| 5,766,640 | 6/1998 | Morris, Jr. et al. .................... 514/878 |

FOREIGN PATENT DOCUMENTS

| | | | |
|---|---|---|---|
| 2432869 | 3/1980 | France . | |
| 946545 | 7/1982 | U.S.S.R. .............................. | 424/717 |

OTHER PUBLICATIONS

A. Goulding et al vol. 133, May 1985 pp. 891–893.
J. Lemann, Jr. et al Abstract A.C.N. Dec. 7–10, 1986.
Ballina et al J. Andocrinol. Invest. 8; 171–173(1985).
Lemann, Jr. et al Kidney Inter. 31(1) 353 1987.
Chem. A b. 2148 F Wolf et al Chem. AB.
New England J. of Med. vol. 330 Jun. 23, 1994 1776–1781.
Lemann, Jr. et al Kidney International 1989 pp. 688–693.
Burnell, *Am. J. Physiol.* 250:F302–F307 (1986).
Kocian et al., *Nutr. Metab.* 23:391–398 (1979).
Orsatti et al., *Calcif. Tissue Res.* 21:195–205 (1976).
Pacifici et al., *N. Engl. J. Med.* 31:1025 (Oct. 1987).
Richards et al., *Lancet* 2:994 (1972).
Stacy et al., *J. Physiol.* 210:549–564 (1970).
Wachman et al., *Lancet* 2:958–959 (1968).
"Osteoporosis" in *Diet and Health Implications for Reducing Chronic Disease Risk*, Natl. Res. Council, Ch. 23 (1989).
Dietz, et al., *Clin. Sci.* 61:69S–71S (1981).
Orsatti, 86 *Chem. Abstr.* 41549e (1976).
Goldsmith et al., *J. Clin. Endo. Metab.* 43:523–532 (1976).
Silverberg et al., *J. Bone and Mineral Res.* 1(4):383–388 (1986).
Lutz, *Am. J. Clin. Nutr.*, 39:281, (Feb. 1984).
Sakhaeee et al., *Kidney Int.* 24:348 (1983).
Seeman et al., *N. Eng. J. Med.* 320:554–558 (1989).
Ballina et al., *J. Endocrinol Invest.* 8:171–174 (1985).
Barzel et al., *Clin. Sci.* 36:517–524 (1969).
Barzel, In: Barzel, U.S., ed. *Osteoporosis*: 199–206, (1970).
Barzel, *Am. J. Clin. Nutr.* 23(6): 833–840 (Jun., 1970).
Barzel, *Arch Phys. Med. Rehabil.* 52(3): 135–137 (Mar., 1971).
Barzel, *Israel Journal of Medical Sciences* 7:499 (1972).
Barzel, *Calcif. Tissue Res.* 21 Suppl: 417–422 (Aug., 1976).
Barzel, *Semin. Nucl. Med.* 17(4): 283–292 (Oct., 1987).

*Primary Examiner*—Thurman K. Page
*Attorney, Agent, or Firm*—Townsend and Townsend and Crew LLP

[57] ABSTRACT

Novel methods are provided for treating osteoporosis in humans, comprising administering therapeutic amounts of pharmaceutically-acceptable alkalinizing salts of potassium. The preferred salt is potassium bicarbonate. The methods may also be used to prevent or delay the onset of osteoporosis. Dietary supplementation is a preferred and convenient method of administration.

24 Claims, 2 Drawing Sheets

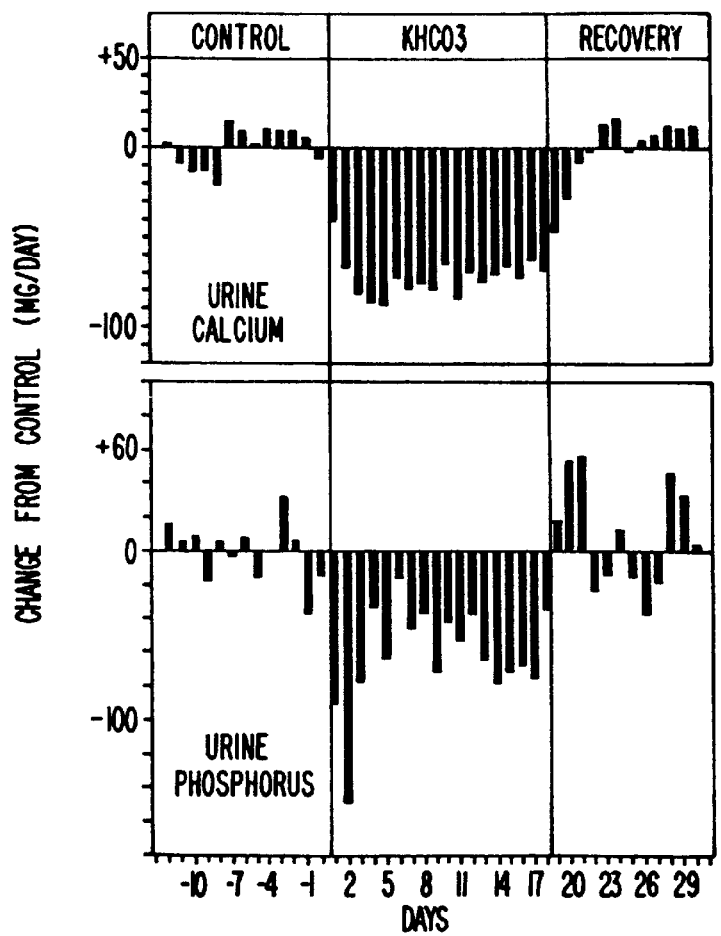
FIG._1.
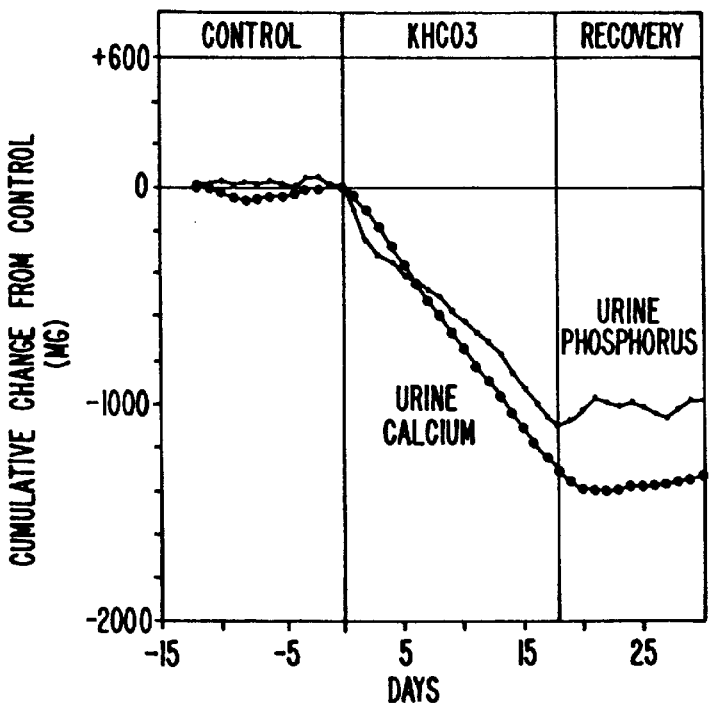
FIG._2.

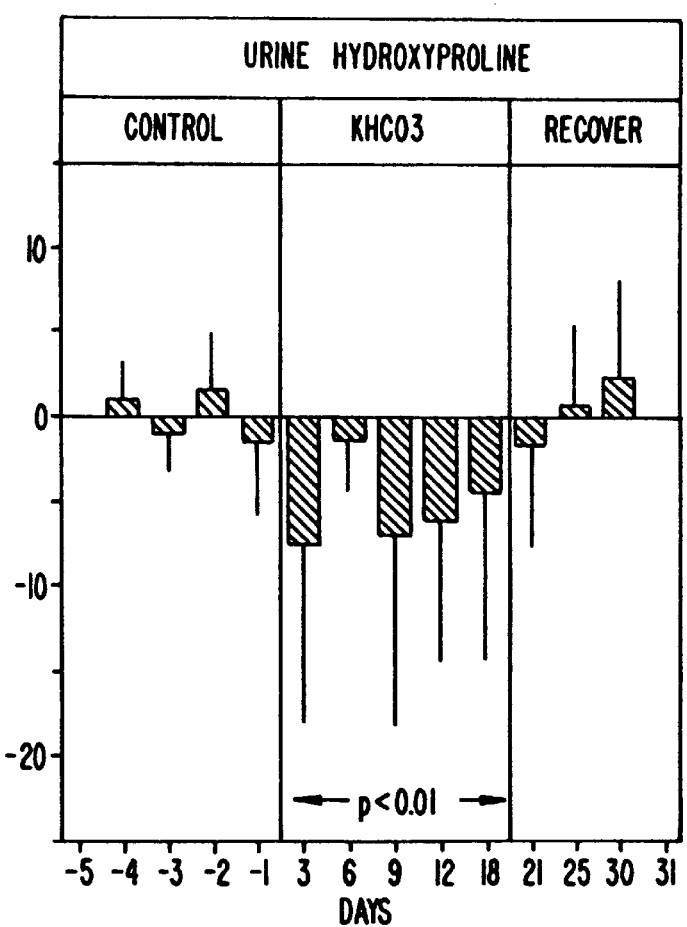
FIG._3.
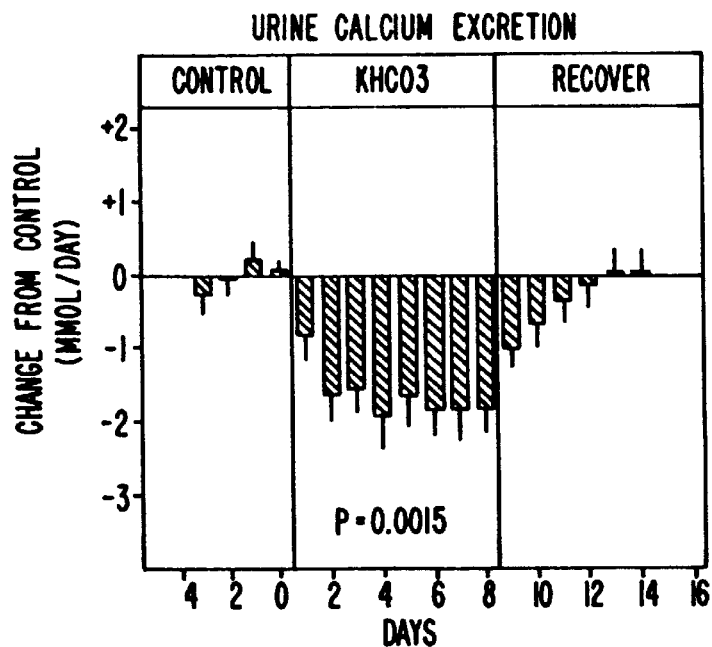
FIG._4.

6,027,737

TREATMENT FOR OSTEOPOROSIS USING POTASSIUM SALTS

CROSS-REFERENCE TO RELATED APPLICATION

This is a Continuation of application Ser. No. 08/023,744, filed Feb. 25, 1993, now abandoned which is a continuation of application No. 07/805,673 filed Dec. 12, 1991 abandoned, which is a continuation of U.S. patent Ser. No. 07/420,597, filed Oct. 17, 1989, now U.S. Pat. No. 5,171, 583, which is a continuation-in-part of U.S. patent application Ser. No. 07/260,856, filed Oct. 21, 1988, now abandoned, the complete disclosures of which are incorporated herein by reference.

GOVERNMENT SUPPORT

This invention was made with Government Support under Grant No. M01-RR0079 awarded by the National Institutes of Health. The Government has certain rights in this invention.

FIELD OF THE INVENTION

This invention concerns novel methods for treating osteoporosis in humans and, more particularly, involves the administration of pharmaceutically acceptable alkalinizing potassium salts, such as potassium bicarbonate, in a variety of dietary and pharmaceutical compositions.

BACKGROUND OF THE INVENTION

Osteoporosis is a metabolic bone disease characterized pathologically by an absolute decrease in the amount of bone, and clinically by increased susceptibility to fractures. Riggs et al., N. Engl. J. Med. (1986), 314:1676; Rusbach et al., In: Textbook of Endocrinology, Ed(s) Williams, (1981), p. 922; Riggs, In: Cecil Textbook of Medicine, Ed(s) Wyngaarden et al., (1985), p. 1456; Riggs et al., Am. J. Med., (1983), 75:899.

In post-menopausal women, estrogen deficiency has been identified as a major predisposing factor. Recent studies in normal women ages 20 to 88 years indicate, however, that substantial bone loss from the axial skeleton occurs gradually in the decades before estrogen deficiency ensues at menopause. Riggs et al., J. Clin. Invest., (1986), 77:1487. According to Riggs et al., " . . . factors in addition to estrogen deficiency must contribute to the pathogenesis of involutional osteoporosis in women because about half of overall vertebral bone loss occurs premenopausally." (Id.).

Calcium deficiency is believed to be one of those additional factors. Riggs, In Cecil Textbook of Medicine, Id.; Nordin, (1985), Lancet 2:720; Fujita, (1986), 12:49; Heaney, In: Osteoporosis II Ed(s), Bonzel, (1979), p. 101; and Heaney, (1982), J. Lab. Clin. Med. 100:309. Three conditions, in turn, have been identified as predisposing to calcium deficiency: suboptimal calcium intake, subnormal intestinal calcium-absorptive ability and normal or above average protein intake, Heaney, In Osteoporosis II, Id.; Heaney et al., (1982), Am. J. Clin. Nutr. 36:986.

More than 50% of women in the United States ingest less calcium than is recommended (Recommended Dietary Allowance [RDA]) by the National Research Council. Committee on Dietary Allowances, Food and Nutrition Board: Recommended Dietary Allowances, 9th Ed. (1980). In postmenopausal women, the difference between actual and optimal calcium intake is underestimated, since the recommended intakes do not take into consideration that intestinal calcium absorptive ability ordinarily declines with age. Heaney et al., Id.; Avioli, et al., (1965), J. Clin. Invest., 44:1960; Bellamore et al., (1970), Lancet, 2:535; Alevizaki, et al., (1973), J. Nucl. Med. 14:760; and Gallagher et al., (1979), J. Clin. Invest. 64:729. At sub-RDA and RDA levels of calcium intake, calcium balance (calcium intake less calcium excretion) is negative in apparently normal adults over a wide span of ages. Lutz, (1984), Am. J. Clin. Nutr. 39:281.

An increasing demand on body calcium stores is imposed by increasing dietary protein, which increases urinary excretion of calcium. Lutz, Id.; Schuette, et al., (1982), J. Nutr. 112:338; Lutz, et al., (1981), Am. J. clin. Nutr., 34:2178; Hegsted, et al., (1981), J. Nutr. 111:553; Schuette, et al., (1980), J. Nutr. 110:305; Allen, et al., (1979), 32:741; and Margen, et al., (1974), Am. J. Clin: Nutr. 27:584. Intestinal absorption of calcium fails to increase commensurately with protein-induced calciuria, hence external calcium balance becomes negative. Lutz, Id.; Schuette, et al., (1982), Id. In combination, low dietary intake of calcium and high dietary intake of protein result in greater calcium deficiency than does either condition alone. Lutz, Id.; and Rekha, et al., 1974, J. Nutr. 104:695.

It has been reported that substitution of sodium bicarbonate for an equivalent amount of sodium chloride in the diet could reverse the negative calcium balance that occurs in women (including post-menopausal women) who are in negative calcium balance on a regimen of average calcium and moderately increased protein intake. Lutz, Id. The bicarbonate-induced improvement in calcium balance occurred with unchanged calcium intake. The observations of Lutz introduce the component of acid-base balance as a potential regulatory factor in calcium balance in normal subjects and raises important questions concerning the potential role of acid-base factors in the pathogenesis of involutional osteoporosis.

More recently, it has been reported that potassium bicarbonate, but not sodium bicarbonate, reduces urinary calcium excretion and improves calcium balance in healthy young men; specifically, the external calcium balance was rendered less negative. Lemann, et al., (1989), Kidney Int. 35:688. Based upon the data obtained, it was suggested that the potassium bicarbonate may have been deposited as bone carbonate. Analysis of urinary hydroxyproline excretion did not provide evidence of reduced bone resorption, although inhibition of bone resorption could not be excluded; the measured change in calcium balance was small. Finally, the possibility that $KHCO_3$ administration may have acted to stimulate bone formation was not evaluated. Lehmann et al., Id., at 694.

It has also been noted in the literature that the administration of other alkalinizing potassium supplements induces a decrease in urinary calcium excretion (Sakhaee, et al., (1983), Kidney Int. 24:348). In this study it was shown that sodium citrate failed to significantly reduce urinary calcium excretion, while the administration of potassium citrate was attended by a significant decline in urinary calcium levels.

It is among the objects of the present invention to provide a method which is not only useful for reducing calcium excretion and thereby improving calcium balance, but which decreases bone resorption and conserves and/or increases bone mass in both normal and osteoporotic patients.

SUMMARY OF THE INVENTION

The present invention involves a novel method for ameliorating or preventing osteoporosis in humans afflicted with or predisposed to osteoporosis, which comprises administering a therapeutically- or prophylactically-effective amount of a composition of a pharmaceutically-acceptable alkalinizing potassium salt. The potassium salt may be selected from the group consisting of potassium bicarbonate, and potassium salts of carboxylic acids such as potassium acetate, potassium gluconate, and potassium citrate, among others. The use of potassium bicarbonate is particularly preferred.

The potassium salt may be administered to ameliorate or prevent osteoporosis in any of several therapeutically- or prophylactically-acceptable forms and by a variety of routes. The compositions may conveniently be formulated and administered as a dietary supplement. An effective dosage of potassium bicarbonate is typically about 50–250 millimoles (mmoles) per 70 kg body weight per day.

DESCRIPTION OF THE DRAWING

FIG. 1 is a graph showing the effect of $KHCO_3$ on urine calcium and phosphorus excretion in postmenopausal women. Bars represent the change for the average excretion levels in a control period in which the $KHCO_3$ was not administered, with bars extending below the zero reflecting a decrease in excretion, and bars extending above the zero line reflecting an increase in excretion;

FIG. 2 is a graph similar to FIG. 1, showing the cumulative change in excretion from the average excretion in the control period;

FIG. 3 is a similar graph, showing the effect of $KHCO_3$ on urine hydroxyproline excretion in postmenopausal women. (Hydroxyproline is a biochemical marker of bone resorption rate); and FIG. 4 is a graph similar to FIG. 1, showing the effect of $KHCO_3$ on urine calcium excretion in healthy young men.

DESCRIPTION OF THE PREFERRED EMBODIMENTS

In accordance with the present invention, novel methods are provided for preventing or ameliorating osteoporosis, which comprise administering to subjects an alkalinizing potassium salt, e.g., potassium bicarbonate, in amounts sufficient to provide the desired physiological benefit while avoiding amounts sufficient to induce undesirable toxic effects.

As used herein, the terms "treatment" or "treating" cover any treatment of osteoporotic disease, and include: (1) preventing osteoporosis from occurring in a subject who may be predisposed to the disease but has not yet been diagnosed as having it; (2) inhibiting the disease, i.e., arresting its development; or (3) ameliorating or relieving the symptoms of the disease, i.e., causing regression of the osteoporotic state.

Osteoporosis is a relatively common disease and has been the subject of intensive investigation. A variety of specific pharmacologic agents have been developed to treat the disease, Spector, et al., (1989), Drugs, 37:205; and Ettinger, (1988), West. J. of Med., 149:691. In addition, the administration of dietary calcium supplements has long been advocated, but it has been shown to be of limited if any effect. Id.

One hypothesis of the mechanism responsible for the advantageous results obtained by the present invention is as follows. First, the administration of potassium bicarbonate may correct an underlying state of systemic metabolic acidosis that is ordinarily accompanied by positive acid balance (i.e., continuing acid retention in the body) which may cause a continuing abnormal rate of dissolution of bone mineral. Correction of systemic metabolic acidosis may thus arrest the abnormal rate of bone mineral dissolution and effect remineralization. Second, at the same time the administration of potassium bicarbonate avoids the calciuric effect that the administration of a sodium alkalinizing salt would entail, the anticalciuric effect of the bicarbonate thus being unopposed by the calciuric effect of sodium, and enhancing bicarbonate-induced calcium retention in the body. Third, the administration of potassium bicarbonate may lessen urinary excretion of phosphorus, by promoting retention of phosphorus by the kidney. Phosphorus, like calcium, is an important mineral constituent of bone. See generally Kurtz I., Mather T., Hulter H. N.; Schambelan, M.; and Sebastian, A., "Effect of diet on plasma acid-base composition in normal human," Kidney Int. 24:570–680, 1983; Sebastian A, Hernandez, R. E., Portale A. A., Colman J., Tatsuno J., and Morris R. C. Jr., "Normal variations of diet potassium influence set-point at which kidneys maintain serum phosphorus concentration." Kidney Int. 35:387, 1989.

It will be understood that the mechanisms hypothesized above, while consistent with known data, should not be construed as limiting the present invention.

It is believed that administration of the alkalinizing potassium salts conserve and/or increase bone mass in both osteoporotic and potential osteoporotic patients. Thus, it has been demonstrated that daughters of women with osteoporosis have reduced bone mass in the lumbar spine and perhaps in the femoral neck; that reduction in bone mass may put them at risk for fractures. Seeman E., Hopper J. L., Bach L. A., Cooper M. E., Parkinson E., McKay J., Jerums G.: Reduced bone mass in daughters of women with osteoporosis. *N. Engl. J. Med.* 320:554–558, 1989. Use of the potassium salt therapy of this invention with these subjects may delay if not prevent the onset of osteoporosis and may decrease its severity.

The alkalinizing potassium salts which may be employed in the process of the present invention are those which exhibit the ability to improve the calcium balance, decrease bone resorption, and conserve and/or increase bone mass in an individual, without significant undesirable side effects. By an alkalinizing salt is meant one which, when present in the body fluids, produces hydroxyl ions or consumes hydrogen ions and is thereby capable of reducing the acidity of tissue fluids or urine. A number of pharmaceutically-acceptable salts are known, several of which are set forth in Berge et al., J. Pharmaceut. Sci. (1977) 66:1, which is incorporated herein by reference. Given the disclosure herein, it will be well within the ability of one skilled in the art to select and screen pharmaceutically-acceptable potassium salts for the ability to treat osteoporosis using well known methods and techniques. Desirably, a potassium salt will be selected which is therapeutically effective in amounts readily achievable in humans while being relatively well-tolerated. Different salts may be chosen depending on particular routes of administration and preferred modes of formulation.

The potassium salts which may be thus administered are suitably selected from the group consisting of potassium bicarbonate ($KHCO_3$), and potassium salts of carboxylic acids which alkalinize in vivo and generate bicarbonate ion as a metabolite after ingestion, e.g., potassium gluconate ($C_6H_5K_3O_7$) and potassium citrate ($C_6H_{11}KO_7$). The use of potassium bicarbonate is particularly preferred.

The preparation, isolation and purification of these compounds are well known to those skilled in the art, as the salts are commonly employed in a therapeutic setting for a variety of uses other than described herein. Specific preparation procedures for each salt are described in general terms in Remington's Pharmaceutical Sciences, Mack Publishing Company, Easton, Pa., 16th Ed., 1982, which is incorporated herein by reference.

Administration of an alkalinizing potassium salt as an active compound may be in a pharmaceutical composition described hereinafter and can be via any of the accepted modes of administration for agents which are known to affect osteoporosis. These methods include oral, parenteral, and other modes of systemic administration. Different alkalinizing potassium salts may be admixed and simultaneously administered, or benefit may be gained in some instances by their separate, sequential administration.

Depending on the intended mode, the compositions may be in the form of solid, semi-solid or liquid dosage forms, such, for example, as tablets, capsules, pills, powders, granules, crystals, liquids, suspensions, or the like, preferably in unit-dosage forms suitable for administration of relatively precise dosages. The compositions may include a conventional pharmaceutical carrier or excipient and, in addition, may include other medicinal agents, pharmaceutical agents, carriers, etc.

The amount of the alkalinizing potassium salt administered in accordance with the present invention will, of course, be dependent on the subject being treated, the severity of the affliction, the manner of administration, and the judgment of the prescribing physician. However, an effective dose of potassium bicarbonate, for instance, will be in the range of 40–400 mmoles/70 kg/day, preferably 40–250 mmoles/70 kg/day. Dosages may be adjusted by monitoring the effects of the amount administered and adjusting subsequent amounts as appropriate.

Many of the potassium salts of the invention may be administered in relatively large amounts without serious side effects, although indiscriminate use of potassium salts may produce toxic manifestations of hyperkalemia and gastrointestinal irritation. In cases where the compound is administered to prevent the emergence of osteoporosis in subjects susceptible to osteoporosis, or to those suffering from only mild or borderline osteoporosis, the dose may be adjusted accordingly to lower maintenance levels.

For solid compositions, the alkalinizing potassium salts such as potassium bicarbonate may be provided separately or may be compounded with conventional nontoxic solid carriers such as, for example, pharmaceutical grades of mannitol, lactose, starch, magnesium stearate, talcum, cellulose, glucose, sucrose, magnesium carbonate, and the like. Liquid pharmaceutically-administrable compositions can, for example, be prepared by dissolving the salt, such as potassium bicarbonate, and optional pharmaceutical adjuvants in a carrier such as, for example, water, aqueous dextrose, glycerol, and the like, to thereby form a solution or suspension. If desired, the pharmaceutical composition to be administered may also contain minor amounts of nontoxic auxiliary substances such as pH buffering agents and the like, for example, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, supra. The composition or formulation to be administered will, in any event, contain a quantity of the alkalinizing potassium salt in an amount effective to maintain bone mass and alleviate or ameliorate the symptoms of osteoporosis or prevent their emergence in the subject being treated.

For oral administration, a pharmaceutically-acceptable nontoxic composition is formed by the incorporation of any of the normally employed excipients such, for example, as pharmaceutical grades of mannitol, lactose, starch, magnesium stearate, talcum, cellulose, glucose, sucrose, magnesium carbonate, and the like. Such compositions take the form of solutions, suspensions, tablets, pills, capsules, powders, granules, crystals, sustained-release formulations, and the like. Such compositions may contain about 10–100% active ingredient, preferably about 25–90%. As a dietary supplement potassium bicarbonate, for example, may be supplied as granules or powder and applied directly to foodstuffs or dissolved in drinking water as a convenient means of administration.

The methods of the invention may also find use in identifying or otherwise diagnosing subjects who would benefit from the treatment methods disclosed herein. More particularly, an individual's excretion in the urine of a bone resorption factor, such as hydroxyproline, and/or excretion of urine calcium is determined as a baseline level. An alkalizing potassium salt, such as potassium bicarbonate, is then administered according to the methods described herein. Typically the salt will be administered in an amount and for a time sufficient to detect a lowering of the urine component which is being monitored in individuals with osteoporosis or susceptible to osteoporosis and who may ultimately be treatable with the therapeutic methods described. If the subject is thereby identified as having a decrease in the urinary component being monitored from their baseline level, a physician may then elect to initiate an appropriate therapy or to further evaluate the subject.

The following examples illustrate some particularly preferred, non-limiting embodiments of the invention.

EXAMPLE 1

Effect of Potassium Bicarbonate on Urine Calcium Excretion and Bone Resorption in Post-Menopausal Women In six post-menopausal women who were not hypertensive, it was found that administration of potassium bicarbonate, 120 mmoles per kg body weight per day for 18 days, caused a significant and sustained reduction in urine calcium and phosphorus excretion rates (see FIGS. 1 and 2) and in the urinary excretion rate of a biochemical marker of bone resorption rate (see FIG. 3).

The studies were performed while the patients resided in the University of California General Clinical Research Center (Moffitt Hospital). Throughout the period of residence, the patients ate a constant diet of known composition, comprising (per 60 kg body weight) 546 mg calcium, 948 mg phosphorus, 60 Meq sodium, and 56 meq potassium. A supplement of sodium chloride of 60 mmoles/day was provided, making total intake 120 meq per 60 kg body weight per day. Fluid intake was fixed.

The subjects were allowed 10 days for their bodies to equilibrate and adapt to the fixed diet. Then, following immediately and in succession, the subjects underwent a 12-day control period (CONTROL) prior to initiation of $KHCO_3$ administration, an 18-day period of $KHCO_3$ administration, and a 12-day recovery period after discontinuation of $KHCO_3$.

FIG. 1 shows the changes in urine calcium excretion (upper panel) and urine phosphorus excretion (lower panel) for the group of six subjects. For each subject, the average value of calcium excretion for the entire CONTROL period was subtracted from each day's calcium excretion, thereby generating a "difference from CONTROL" value for every day of the study, including the individual CONTROL days. For each day of the study, the average of the daily "differences from CONTROL" were calculated for the entire group of six subjects, and those were plotted in the figures on vertical bars. Vertical bars extending below the zero line represent decreases in calcium excretion relative to the average control value, vertical bars extending above the zero line represent increases in calcium excretion relative to the control value. A similar procedure was used for displaying the effects on urine phosphorus excretion (FIG. 2) and on urine hydroxyproline excretion (FIG. 3).

Note that $KHCO_3$ administration resulted in a prompt and sustained reduction in both urine calcium and phosphorus excretions, and that after discontinuation of $KHCO_3$, the excretion rates of those substances gradually returned to control. Calcium excretion in the feces increased slightly with potassium bicarbonate, but not to the extent that urine calcium excretion decreased, with the result that calcium balance was increased in the direction of net calcium retention by the body.

A similar phenomenon of $KHCO_3$-induced reduction in urine excretion rate was observed for urine hydroxyproline excretion (FIG. 3).

EXAMPLE 2

Effect of Potassium Bicarbonate on Urine Calcium Excretion of Normal Men

Rigorously controlled metabolic balance techniques were used to study the effect of oral administration of potassium bicarbonate, 150 meq/70 kg/day, on urine calcium excretion in six healthy men eating a constant acid-producing diet.

For each subject the difference of each day's urine calcium excretion from the average calcium excretion during the entire control period for that subject was computed. The average of those daily differences for the group of six subjects was determined.

Urine calcium excretion was observed to decrease promptly on initiation of the $KHCO_3$ treatment and remained lower throughout the period of $KHCO_3$ administration. The magnitude of reduction, about 2 mmole/day, is equivalent to about 80 mg/day. The results are shown in FIG. 4.

From the foregoing, it will be appreciated that the present invention provides methods which effectively treat/prevent osteoporosis in human subjects. Since many of the alkalinizing potassium salts such as potassium bicarbonate are naturally-occurring and readily available, their use as a dietary supplement or otherwise presents the possibility of a purely nutritional approach to osteoporosis, thereby avoiding the disadvantages of conventional pharmacological intervention.

Although the present invention has been described in some detail by way of illustration and example for purposes of clarity and understanding, it will be obvious that certain changes and modifications may be practiced within the scope of the appended claims.

What is claimed is:

1. A method for treating osteoporotic disease in a human being subject thereto, which comprises orally administering to such a person a composition containing at least one active ingredient for treating osteoporotic disease, said ingredient being a pharmacologically acceptable potassium salt of a carbohydrate based or citrate based carboxylic acid which generates or is metabolized to the bicarbonate ion after ingestion and is thus capable of reducing acidity in vivo, and being substantially free of sodium bicarbonate, and said composition being administered in an amount sufficient to improve calcium and phosphorus balances and decrease bone resorption and conserve and/or increase bone mass, but not sufficient to induce undesirable toxic effects.

2. The method of claim 1, wherein the potassium salt is administered in an amount of from about 40–400 mmoles/70 kg body weight/24 hours or at a lower maintenance level for preventing the emergence of osteoporotic disease in a person susceptible to osteoporotic disease or for treating a person suffering from only mild or borderline osteoporotic disease.

3. The method of claim 1, wherein the potassium salt is administered in an amount of from about 40–250 mmoles/70 kg body weight/24 hours or at a lower maintenance level for preventing the emergence of osteoporotic disease in a person susceptible to osteoporotic disease or for treating a person suffering from only mild or borderline osteoporotic disease.

4. The method of claim 1, which comprises treating a patient who has osteoporosis or a person who is susceptible to it with said composition.

5. The method of claim 1, wherein the alkalinizing potassium salt is substantially the only active ingredient in the composition for treating osteoporotic disease.

6. The method of claim 1, wherein the composition is administered as a dietary supplement.

7. The method of claim 1, wherein the composition includes a pharmaceutically-acceptable carrier.

8. The method of claim 1, wherein the potassium salt is potassium citrate.

9. The method of claim 1, wherein the potassium salt is administered in an amount of from about 40–400 mmoles/70 kg body weight/24 hours or at a lower maintenance level for preventing the emergence of osteoporotic disease in a person susceptible to osteoporotic disease or for treating a person suffering from only mild or borderline osteoporotic disease.

10. The method of claim 1, wherein the potassium salt is administered in an amount of from about 40–250 mmoles/70 kg body weight/24 hours or at a lower maintenance level for preventing the emergence of osteoporotic disease in a person susceptible to osteoporotic disease or for treating a person suffering from only mild or borderline osteoporotic disease.

11. The method of claim 1, which comprises treating a patient who has osteoporosis or a person who is susceptible to it with said composition.

12. The method of claim 1, wherein the potassium salt is substantially the only active ingredient in the composition for treating osteoporotic disease.

13. The method of claim 1, wherein the composition is administered as a dietary supplement.

14. The method of claim 1, wherein the composition includes a pharmaceutically-acceptable carrier.

15. A method for treating osteoporotic disease in post-menopausal women, which comprises orally administering to such a person a composition containing at least one active ingredient for treating osteoporotic disease, said ingredient being a pharmacologically acceptable potassium salt of a carbohydrate based or citrate based carboxylic acid which generates or is metabolized to the bicarbonate ion after ingestion and is thus capable of reducing acidity in vivo, and being substantially free of sodium bicarbonate, and said composition being administered in an amount sufficient to improve calcium and phosphorus balances and decrease bone resorption and conserve and/or increase bone mass, but not sufficient to induce undesirable toxic effects.

16. The method of claim 15, wherein the potassium salt is administered in an amount of from about 40–400 mmoles/70 kg body weight/24 hours or at a lower maintenance level for preventing the emergence of osteoporotic disease in a person susceptible to osteoporotic disease or for treating a person suffering from only mild or borderline osteoporotic disease.

17. The method of claim 15, wherein the potassium salt is administered in an amount of from about 40–250 mmoles/70 kg body weight/24 hours or at a lower maintenance level for preventing the emergence of osteoporotic disease in a person susceptible to osteoporotic disease or for treating a person suffering from only mild or borderline osteoporotic disease.

18. The method of claim 15, which comprises treating a patient who has osteoporosis or a person who is susceptible to it with said composition.

19. The method of claim 15, wherein the alkalinizing potassium salt is substantially the only active ingredient in the composition for treating osteoporotic disease.

20. The method of claim 15, wherein the composition is administered as a dietary supplement.

21. The method of claim 15, wherein the composition includes a pharmaceutically-acceptable carrier.

22. The method of claim 15, wherein the potassium salt is potassium citrate.

23. The method of claim 1, wherein the potassium salt is potassium citrate or potassium gluconate.

24. The method of claim 15, wherein the potassium salt is potassium citrate or potassium gluconate.

\* \* \* \* \*